(12) United States Patent
Chen et al.

(10) Patent No.: US 7,576,865 B2
(45) Date of Patent: Aug. 18, 2009

(54) OPTICAL COHERENT TOMOGRAPHIC (OCT) IMAGING APPARATUS AND METHOD USING A FIBER BUNDLE

(76) Inventors: Zhongping Chen, 45 Urey Ct., Irvine, CA (US) 92617; Tuqiang Xie, 5234 Michelson Dr., 25B, Irvine, CA (US) 92612; David Mukai, 114a Cabrillo St., Costa Mesa, CA (US) 92627; Matthew Brenner, 15 Woodflower, Irvine, CA (US) 92612

( * ) Notice: Subject to any disclaimer, the term of this patent is extended or adjusted under 35 U.S.C. 154(b) by 550 days.

(21) Appl. No.: 11/405,812

(22) Filed: Apr. 17, 2006

(65) Prior Publication Data
US 2007/0038119 A1 Feb. 15, 2007

Related U.S. Application Data

(60) Provisional application No. 60/672,473, filed on Apr. 18, 2005.

(51) Int. Cl.
*G01B 9/02* (2006.01)
(52) U.S. Cl. ..................................... 356/479
(58) Field of Classification Search ................. 356/479, 356/497
See application file for complete search history.

(56) References Cited

U.S. PATENT DOCUMENTS

| | | | | |
|---|---|---|---|---|
| 5,321,501 A | * | 6/1994 | Swanson et al. | 356/479 |
| 5,921,926 A | * | 7/1999 | Rolland et al. | 600/407 |
| 6,370,422 B1 | * | 4/2002 | Richards-Kortum et al. | 600/478 |
| 7,400,409 B2 | * | 7/2008 | Hauger et al. | 356/479 |

FOREIGN PATENT DOCUMENTS

WO    WO 2004/055570 A2 * 6/2008

* cited by examiner

*Primary Examiner*—Samuel A Turner
(74) *Attorney, Agent, or Firm*—Daniel L. Dawes; Marcus C. Dawes

(57) ABSTRACT

A fiber-optic bundle based optical coherence tomography (OCT) probe method is demonstrated in a multimode optical fiber bundle based OCT system. The system can achieve a lateral resolution of 12 μm and an axial resolution of 10 μm using a super-luminescent diode source. This imaging approach eliminates any moving parts in the probe and has a primary advantage for use in extremely compact and safe OCT endoscopes to image internal organs and great potential to be combined with confocal endoscopic microscopy.

26 Claims, 4 Drawing Sheets

OPTICAL COHERENT TOMOGRAPHIC (OCT) IMAGING APPARATUS AND METHOD USING A FIBER BUNDLE

RELATED APPLICATIONS

The present application is related to U.S. Provisional Patent Application, Ser. No. 60/672,473 filed on Apr. 18, 2005, which is incorporated herein by reference and to which priority is claimed pursuant to 35 USC 119.

GOVERNMENT RIGHTS

The invention was funded in part with a grant from the Department of Defense, Contract FA 9550-04-1-0101, Philip Morris: USA-32598, National Science Foundation (BES-86924) and the National Institutes of Health (EB-00293, NCI-91717, and RR-01192. The U.S. Government has certain rights to the invention.

BACKGROUND OF THE INVENTION

1. Field of the Invention

The invention relates to the field of optical coherence tomography and in particular to optical endoscopic scanning probes used with optical coherence tomographic interferometers.

2. Description of the Prior Art

As a noninvasive imaging technique, optical coherence tomography (OCT) provides high resolution morphological, structural, and functional information in biological tissues. Other noninvasive morphological imaging techniques such as X-ray radiography, magnetic resonance imaging (MRI), computed tomography (CT) and ultrasound imaging have been widely used in various clinical applications with resolutions ranging from 100 µm to 1 mm. However, this resolution is insufficient to delineate the microstructure of biological tissues at the level required to detect many abnormalities, such as early cancers. OCT can achieve an ultrahigh resolution as high as 1 µm in real time, in-situ without specimen removal and processing making it highly attractive for clinical imaging. Since it was first introduced in 1991, OCT has been used to identify microstructures in ophthalmology, skin, oral cavity, respiratory tract, gastrointestinal tract, and bladder. In recent reports, OCT endoscopic and catheter based probes have been developed for clinical use.

To image tissues, movable parts such as MEMS mirrors, MEMS micromotors, linear motors, or rotary fiber joints are used to perform two dimensional imaging or circumferential scanning. Since the mirror size and numerical aperture are limited by the endoscope size, the lateral resolution is subsequently restricted. Three dimensional scanning can be accomplished by repeating the scans with an added directional motion component, but this may be technically challenging in small diameter endoscopic probes, particularly when precisely aligning components. In confined spaces of endoscopic probes, the sweep distances obtainable using MEMS probes may also be quite limited.

Optical coherent tomography (OCT) has been used for high resolution optical imaging in many areas of medicine, especially ophthalmology. The "conventional wisdom" was that OCT could not be done through flexible fiber bundles. The use of flexible fiberoptic bundles to deliver OCT directly to a tissue sample has not been previously achieved.

BRIEF SUMMARY OF THE INVENTION

A fiber-optic imaging bundle for use with an OCT interferometer and scanner is constructed, which is 3.2 mm in diameter, has various lengths, is composed of a large number (here, 50,419 individual fiber cores) of 12 µm fibers. Various lengths of fiber can be used, e.g. 12 inch fibers were used for hamster trachea image, and 6" bundles for an infrared (IR card). Fiber bundles are polished at an angle (8 degrees) at each end to reduce back reflection. The OCT sample light beam is focused by an objective lens to a 10 µm beam spot on the proximal entrance plane of the fiber-optic bundle. The light beam spot is scanned laterally on the entrance plane of the fiber bundle. The light emerging from the fiber cores at the distal end of the fiber bundle is collimated by an achromatic doublet lens and refocused onto the sample by another achromatic doublet lens or GRIN lens. However, the objective lens may not be necessary for images.

The purpose of this system is to provide a means for high resolution imaging biological tissue, which in the illustrated embodiment has transverse and axial resolution of 12 µm and 10 µm, respectively. The fiber-optic bundle can be illuminated at a distance from the light source, and since the scanning mechanism is placed at the proximal end of the fiber, the moving parts of the system are distant from the sample. This bundle allows the creation of a novel high performance endoscope OCT system for imaging of internal organs in two or three dimensions.

The advantage of the fiber-bundle delivery system is to provide ability to image deep internal organs through endoscopes with OCT, and to remove the moving portions of the scanning system from the immediate proximity of the tissues to be imaged, thereby simplifying and streamlining the probe design of a clinical instrument. The system would be useful for in any application of OCT (medical or other) where it would be advantageous to image through a fiber-optic bundle. The invention provides the simplest method for three dimensional OCT imaging in vivo.

The invention will be used to develop clinically useful endoscopic OCT systems that can provide high resolution optical imaging of internal organs and tissues. OCT can penetrate tissues and provide information that conventional endoscopy cannot. This invention allows OCT to be used potentially anywhere that can be accessed by endoscopy. Examples of use include, but are not limited to:
  a. Field of Urology-bladder cancer detection,
  b. Pulmonary Medicine-lung cancer detection and inflammation,
  c. Surgery/minimally invasive surgery-arterial anastomosis,
  d. Cancer detection (cardiac and others),
  e. Gynecological diagnosis (endometriosis, cancer), and
  f. Gastrointestinal-cancer and inflammation detection.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

Figure 1:
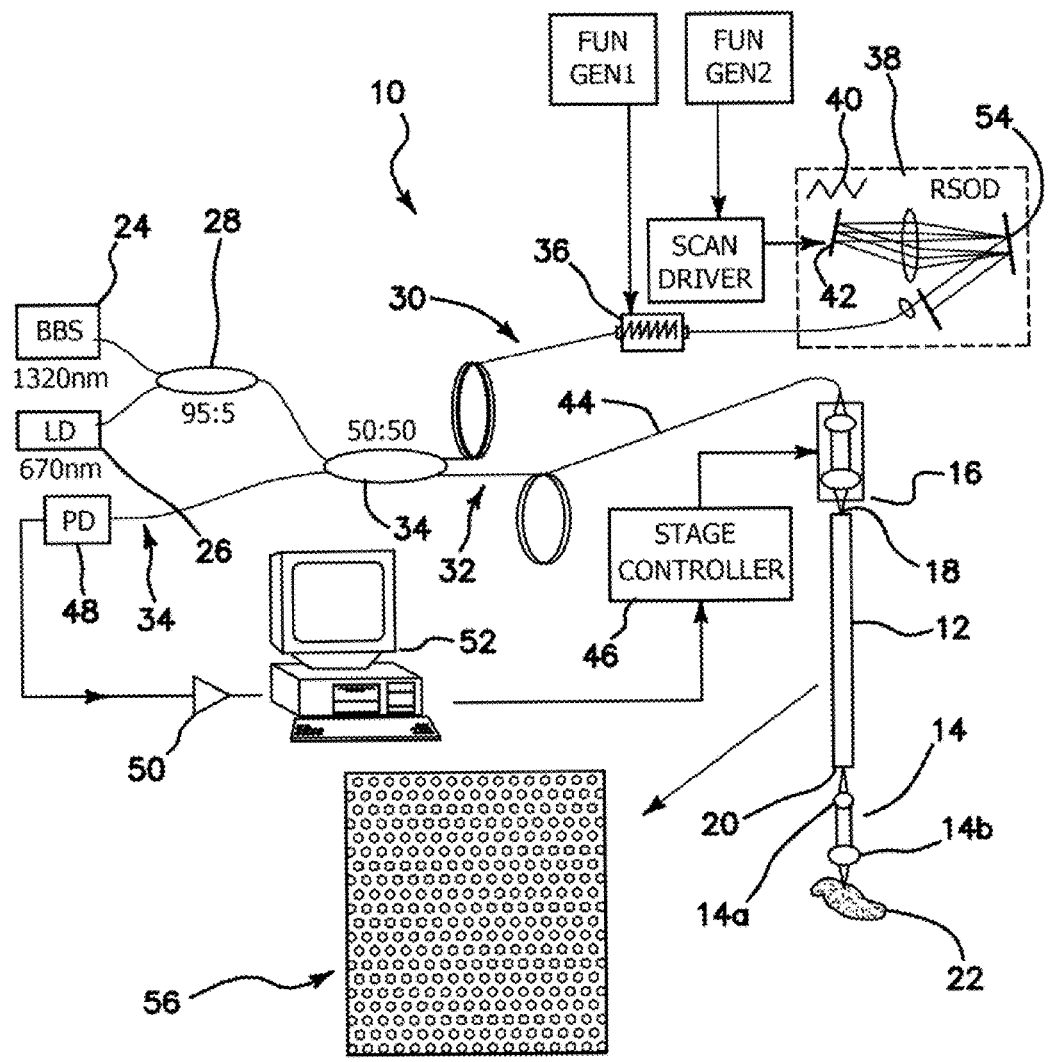
FIG. 1 is a schematic diagram of the OCT system of the invention based on a coherent fiber bundle and microstructure of fiber optic bundle.

In the illustrated embodiment of FIG. 1, we present a new fiber bundle OCT imaging method and apparatus 10 with front view scanning which is comprised of a fused coherent fiber bundle 12 and an objective lens system 14. In this system 10, the scanning mechanism 16 is placed at the proximal fiber bundle entrance 18. The bundle 12, made up of several thousand cores, preserves the spatial relationship between the entrance 18 and the output 20 of the bundle 12. A cross section of the bundle 12 is shown in the enlarged inset 56 of FIG. 1 showing the dense honey-comb packing of the cores. Therefore, one or two directional scanning can be readily performed on the proximal bundle surface 18 to create 2 or 3 dimensional images. Because of this fiber bundle design, the scanning mechanism 16 can be placed proximally and no moving parts or driving current are needed within the endoscope (not shown) in which at least the distal portion of bundle 12 is included with lens system 12. This design is extremely compact, solid and reliable and could be modified for required sizes to perform three dimensional endoscopic imaging of tissue site 22 in a range of clinical settings.

A schematic of the fiber bundle based time-delay superluminescent diode (SLD) OCT system 10 of the illustrated embodiment is shown in FIG. 1. In this case, a superluminescent diode or source 24 with the central wavelength of 1310 nm and the half-maximum-full-width (HMFW) spectral bandwidth of 80 nm was used for illumination. The pigtailed output is 10 mW from this source 24. It must be understood that other light sources may be substituted including broad band coherent or semi-coherent light sources. In addition in the case where the wavelength of source 24 is not in the visible portion of the spectrum, an aiming laser diode 26 in the visible spectrum may also be employed for optical alignment and other purposes which is coupled by a to a combiner 28 with source 24. System 10 is illustrated in the embodiment of FIG. 1 as a fiber optic system, but it may also be implemented if desired to the applicable extent as a free space optical system.

The axial resolution ($\Delta z$) of the OCT system 10 is governed by the coherence length of light source 24 $(2 \ln 2/\pi) \cdot (\overline{\lambda}^2/\Delta\lambda)$ where $\overline{\lambda}$ is the average wavelength, $\Delta\lambda$ is the dispersion or wavelength spread around the average, making the coherence length or axial resolution approximately 9.5 μm. The light is split into reference arm 30 and sample arm 32 by a fiber optic coupler 34. In the reference arm 30 of a fiber optic Michelson interferometer 10, an electro-optic (E-O) phase modulator 36 was inserted into the reference arm 30 prior to rapid scanning optical delay (RSOD) 38. In RSOD 38, a scanning mirror 40 mounted to a galvanometer 42 was set to zero offset to produce a group delay and the E-O modulator 36 provided a stable carrier frequency at 500 KHz for the detection of OCT signal amplitude as per conventional OCT techniques. Reflected signals from sample 22 are combined in coupler 34 with reference the modulated reference signal from reference arm 30. The interference signal is detected by photodetector 48, whose output is amplified and conditioned by amplifier 50 and coupled to computer 52 for OCT data analysis. OCT is well known and an example can be found in U.S. Pat. No. 5,991,697, which is incorporated herein by reference.

In the sample arm 32, the light from the single mode sample fiber 44 was collimated to a Gaussian beam, and focused by an objective lens (20×) 16 to a 10 μm beam spot on the proximal entrance plane 18 of the fiber bundle 12 which was placed at the focal plane of the objective lens 16. The light beam spot driven by a microstage 46 was laterally scanned on the entrance plane 18 of the fiber bundle 12. The light emerging from the single fiber-cores at the distal end face 20 of the fiber bundle 12 was collimated by an achromatic doublet lens 14a and refocused onto the sample 22 by another achromatic doublet lens 14b. Since the light in the fiber bundle 12 is coherent, the individual fibers preserve their relative spatial relationship as the refocused light beam laterally scans the sample 22 corresponding to the same individual fiber scanning position on the proximal entrance 18 of the fiber bundle 12.

The fiber bundles 12 used in the illustrated embodiment are high resolution coherent imaging conduits (Scholt North America, Mass.), each 3.2 mm in diameter, and were studied in varying lengths (25.4 mm, 152 mm and 305 mm). The fiber bundle 12 is composed in the illustrated embodiment of 50,419 individual fiber cores and the external diameter of each individual clad fiber element is 12 μm. The individual fiber core, with a diameter of 9 μm, has a refractive index of 1.58 and a cladding refractive index of 1.48. The numerical aperture (NA) of an individual fiber is 0.55, which is higher than the NA of conventional single mode fiber (0.22). An important quantity in determining which modes of an electromagnetic field will be supported by a fiber is the characteristic waveguide parameter or the normalized wavenumber (V). The V-number of fiber is calculated by $$V = \frac{\pi \cdot d \cdot NA}{\lambda} \quad (1)$$

where λ is the wavelength of light and d is the diameter of fiber core. For our fiber bundle, the V number of the fiber in the fiber bundle is 13.2 for 1300 nm light and much greater than 2.405 which is the maximum V number of the fiber supporting only a single mode. This means that a large number of modes including the fundamental mode will be supported by each fiber in bundle 12. Since the input beam NA of 0.28 of the objective lens 16 to the fiber bundle is less than the individual fiber NA of 0.55, only low-order modes are coupled into and propagate in the individual fibers avoiding the dispersive effect from high order modes. To prevent reflection from the end surfaces 18, 20 of the fiber bundle 12 from overwhelming the signal, it is necessary to polish the fiber bundle end surfaces 18, 20 at an angle of approximately 8° inclined relative to a perpendicular aperture face. This results in near elimination of the reflections at these sites. The transverse magnification ($M_{objective}$) of the lens system 14 in FIG. 1 and the fibers' center-to-center spacing ($\Delta d$) in the fiber bundle 12 determine the lateral resolution ($\Delta r$), which can be estimated by:

$$\Delta r = \frac{\Delta d}{M_{objective}} \quad (2)$$

In our setup, the fibers' center-to-center spacing within the fiber bundle is 12 μm and transverse magnification is close to 1 so that the lateral resolution is approximately 12 μm.

Figure 2A:
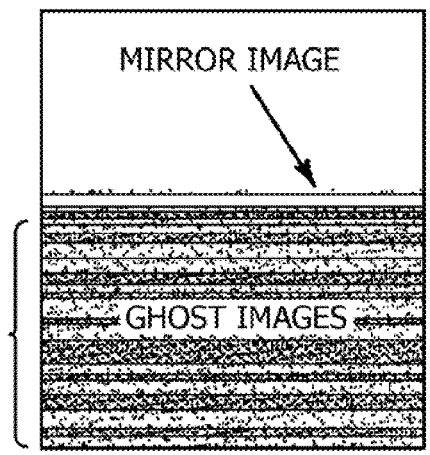
FIGS. 2A-2C are OCT images of a mirror obtained by the OCT system with different fiber bundle lengths, namely FIG. 2A was taken with a system which has a bundle length of 25.4 mm, FIG. 2B with a bundle length of 152 mm and FIG. 2C a bundle length of 305 mm, respectively. The imaging size is approximately 3 mm by 2.8 mm.
Figure 2B:
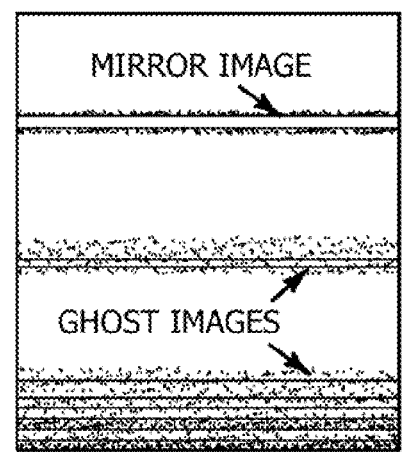
Figure 2C:
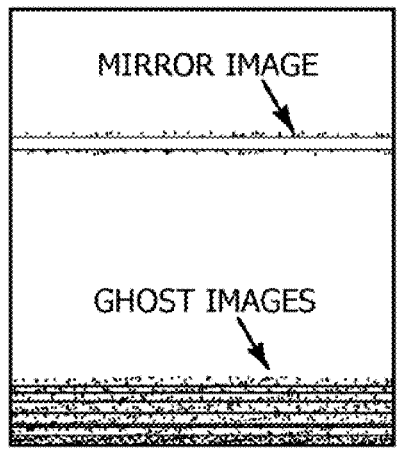

Fiber bundle lengths of 25.4 mm, 152 mm and 305 mm were used to obtain the OCT images shown in FIG. 2A, 2B and 2C, respectively. Ghost images can be seen in FIG. 2A, 2B and 2C. The distance between the fundamental mode light image and the ghost images which are produced by other modes is proportional to the fiber bundle length. The ghost images from top to bottom become weaker in intensity and more dispersive effect is seen. When the bundle length reaches 305 mm, there is one remaining ghost image within the imaging depth range of 2.8 mm, and the fundamental image depth can be more than 1 mm without interruption by the interfering ghost image. If the bundle length is more than 900 mm, the ghost image is out of the display range, and the imaging depth in the fiber bundle OCT system can be 2.8 mm without ghosts which is the standard depth range of conventional tissue OCT systems. Because the diameter of the individual optical fibers is 10 μm, close to the diameter of normal single mode fiber (8 μm) for 1300 nm light, the fundamental mode propagates in the multimode fibers of fiber bundle 12 without extra dispersion as it does in normal single mode fibers.

Figure 3A:
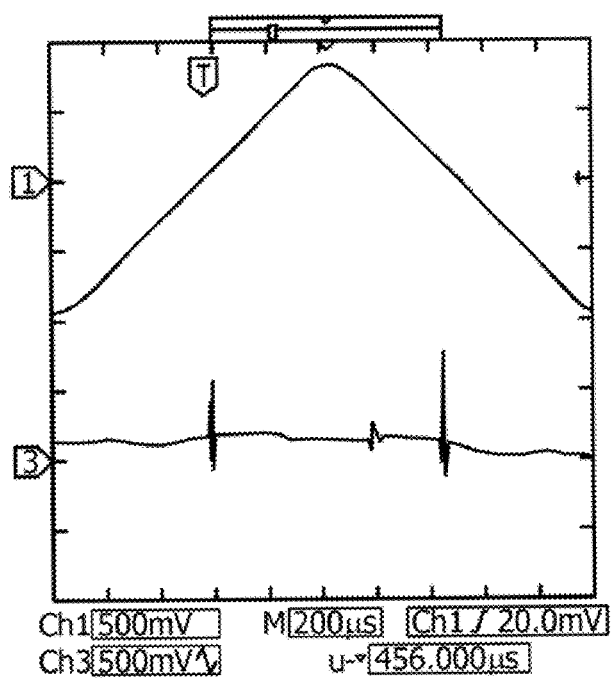
FIGS. 3A and 3B are graphs of an interference fringe signal as a function of time in the time domain in FIG. 3A and as a function of position in the space domain in FIG. 3B.
Figure 3B:
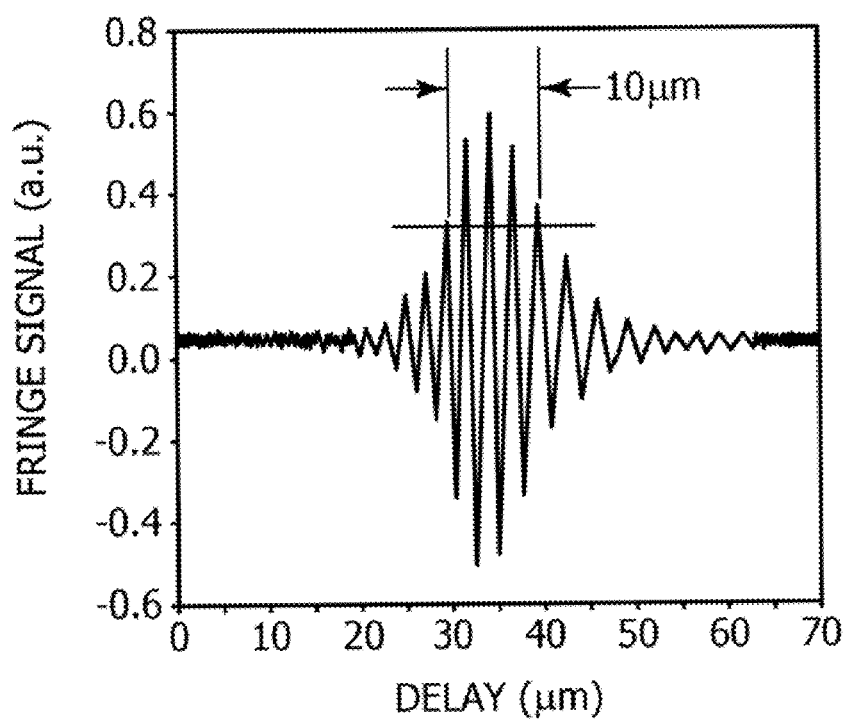

In the OCT image from the fundamental mode in the fiber, the dispersion could almost be compensated as shown in FIG. 3B and the resultant axial resolution is around 10 μm, which is close to coherence length of light source (9.5 μm). During the dispersive compensation, the dispersion of the main interference fringe in the fiber bundle OCT system 10 was compensated by moving the grating 54 in RSOD 38 as it does in a single mode fiber OCT system. See U.S. Pat. No. 6,549,801 for a description of the operation of a single mode fiber OCT system, which patent is incorporated herein by reference.

Figure 4:
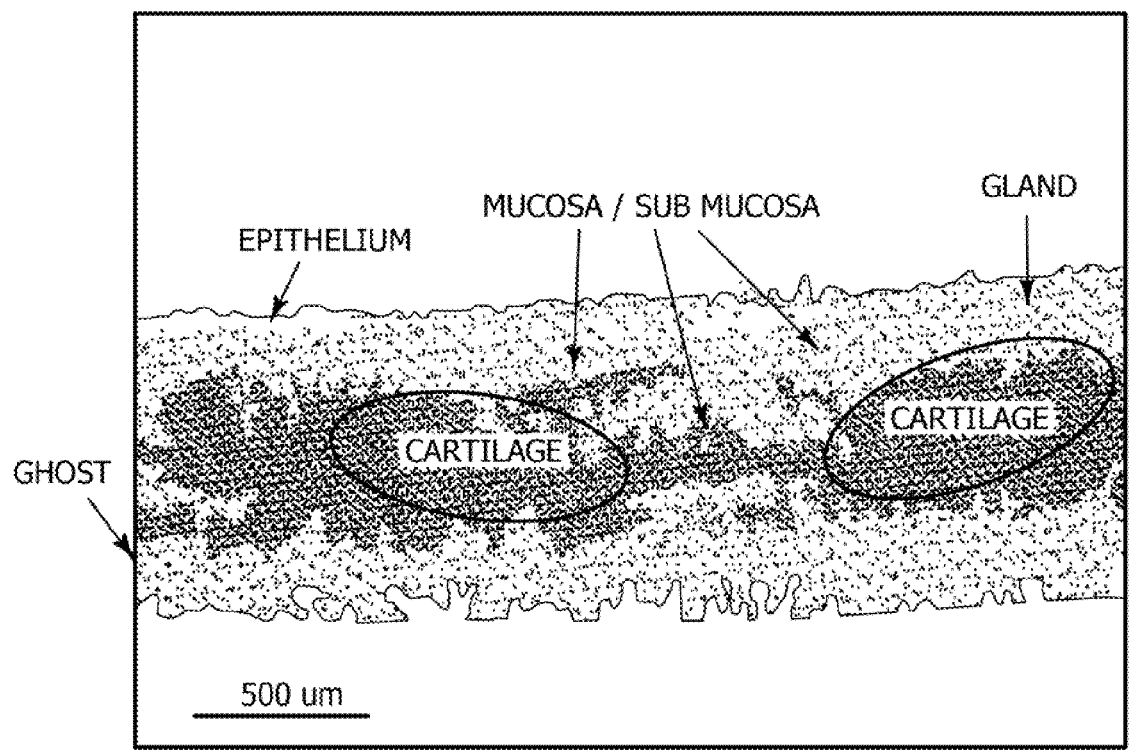
FIG. 4 is a two-dimensional OCT image of a fresh rabbit trachea from a fiber bundle OCT system. The image size is approximately 2.8 mm×2.8 mm. The trachea morphology such as mucosa/submucosa, glands and cartilages can be discerned.

A section of normal fresh trachea was excised from a euthanized rabbit and pinned onto a silicone pad. The sample 22 was scanned by the fiber bundle OCT system 10 and the image shown in FIG. 4 was obtained. The OCT image can delineate the micro morphology of the normal rabbit trachea including mucosa, sub mucosa, glands and cartilage rings as seen in FIG. 4. Compared to the OCT image from a conventional bench top OCT system, the fiber bundle image fidelity, including signal to noise ratio, image depth, and contrast, is slightly degraded.

The image quality degradation may be due to coupling loss between the scanning fiber 44 and the fiber bundle 12. When the focusing beam falls between fiber elements during the lateral scanning beam sweep, the coupling of energy into more than one fiber and into cladding structure results in a coupling loss that degrades the lateral resolution of the fiber bundle OCT system 10. Therefore, the image quality can be significantly improved by minimizing the focusing beam size so that the beam size is less than the individual fiber core size and better coupling of the input beam to each individual fiber core during scanning.

Since the fiber bundle 12 was fine polished for the angle of 8° on each end, the length differences of individual fibers in the fiber bundle 12 are close to the coherence length of the light source and it is not necessary to reconstruct the OCT image. When the length differences of individual fibers are $\Delta L$, the light path difference is $2\Delta n*\Delta L$ for the same axial objective position, where $\Delta n$ is the refractive index difference between the fiber core ($n_{glass} \cong 1.5$) and air ($n_{air} \cong 1$), and where the typical value of $2\Delta n$ is close to 1. If $\Delta L$ is greater than the coherence length of light source 24, the OCT image should be reconstructed in the imaging processing software in computer 52 based on the OCT image of a mirror to cancel the effect of the length differences on imaging.

To improve the imaging fidelity, the coupling efficiency can be increased by a number of means including matching the numerical aperture between the focusing lens system 16 and the bundle 12, as well as optimizing the lens systems and matching the index between optical component connections. In addition, a specially designed fiber coupler, such as 90:10 splitting coupler and circulator, could be used in the system 10 to deliver more power to the sample arm 32 from the light source 24. If two proper graded index (GRIN) lenses replace the two achromatic doublet lenses 14a and 14b, the probe diameter can be made smaller than 1 mm and will be more solid and easier to pack and seal than the OCT probes of the illustrated embodiment.

In summary, what is disclosed is a novel OCT system based on a coherent fiber-optic imaging bundle 12 in which feasibility is demonstrated to image biological tissue at transverse and axial resolution of approximately 12 μm and 10 μm, respectively. Although the fiber bundle 12 is comprised of multimode fibers, due to large differences between the core index and cladding index, the fiber bundle can still be used in the sample arm 32 of the OCT system 10. Enough imaging depth can be achieved to avoid the ghost images from high order modes if the fiber bundle 12 is chosen to be long enough. Since the actual scanning mechanism is placed at the proximal entrance 18 of the fiber bundle 12, it enables simplified two directional scanning. This approach allows the production of a medical or optical probe which can be very safe without any driving current, and which can be extremely compact and solid without any moving parts. This novel fiber bundle 12 based OCT system 10 demonstrates the great potential for a high performance OCT endoscope to image various internal organs in two or three dimensions. This OCT system 10 could be combined with confocal endoscopic microscopy.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following invention and its various embodiments.

Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the invention is explicitly contemplated as within the scope of the invention.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. An improvement in an OCT system for imaging a sample having a sample arm with a scanner, the improvement comprising a fiber optic bundle having a proximal entrance aperture which is optically coupled to the sample arm through the scanner and having a distal exit aperture optically directed to the sample remote from the scanner, wherein the optic fiber bundle has a predetermined optical length chosen to distance a fundamental mode light image from ghost images which are produced by other modes to avoid any overlap of the fundamental mode light image and ghost image.

2. The improvement of claim 1 where the fiber optic bundle is comprised of a plurality of separate single mode or multimode fiber cores.

3. The improvement of claim 2 further comprising scanning optics for focusing a scanning light beam onto the proximal entrance aperture of the fiber optic bundle which is optically coupled to the sample arm through the scanner.

4. The improvement of claim 1 further comprising objective optics for focusing light onto the sample from the distal exit aperture of the fiber optic bundle.

5. The improvement of claim 1 further comprising an endoscopic instrument in which the fiber optic bundle is included.

6. The improvement of claim 2 where the fiber optic bundle maintains relative spatial relationship between the plurality of cores comprising the fiber optic bundle between the proximal entrance aperture and the distal exit aperture of the optic fiber bundle, and where the OCT system comprises a light source characterized by a coherence length and an objective optics coupling light between the distal exit aperture of the fiber optic bundle and the sample, the relative spatial relationship of the light focused by the objective optics onto the sample from the distal exit aperture being maintained when focused onto the sample and spatially corresponds to an individual fiber scanning position on the proximal entrance aperture of the fiber optic bundle.

7. The improvement of claim 3 where the scanning optics and each core is characterized by a corresponding numerical aperture, and where the numerical aperture of the scanning optics is less than the numerical aperture of each core in the fiber optic bundle so that only low-order modes are coupled into the fiber optic bundle and propagate in each core.

8. The improvement of claim 1 where the proximal entrance aperture and distal exit aperture are polished at a predetermined angle to reduce reflection from the entrance aperture and exit aperture.

9. The improvement of claim 8 where the predetermined angle is approximately 8° inclined relative to a perpendicular aperture face.

10. The improvement of claim 1 where the predetermined optical length is chosen to position the ghost images out of the field of view of the fundamental mode light image.

11. The improvement of claim 2 where the scanner provides a scanning beam characterized by a beam size and where each core is characterized by a fiber core size, where the beam size is less than the fiber core size to improve coupling of the scanning beam into each core during scanning.

12. The improvement of claim 1 further comprising means for improving coupling efficiency between the scanner and fiber optic bundle.

13. The improvement of claim 12 where scanner and the fiber optic bundle are each characterized by a corresponding numerical aperture and where the means for improving coupling efficiency comprises means for matching a numerical aperture of the scanner and the fiber optic bundle, means for optimizing a scanning optics and an objective optics, or means for matching index of refraction between optical component connections between the scanner, fiber optic bundle, and an objective optics.

14. The improvement of claim 1 where the OCT system comprises a light source, and an optimized fiber coupler coupled to the light source to deliver increased power to the sample arm from the light source.

15. The improvement of claim 1 further comprising objective optics for optically coupling the distal exit aperture of the fiber optic bundle into the sample and where the objective optics comprises two graded index (GRIN) lenses to reduce probe diameter.

16. An improvement in a method of operating an OCT system for imaging a sample, the OCT system having a sample arm with a scanner, the improvement comprising:

optically coupling the sample arm through the scanner to a fiber optic bundle through a proximal entrance aperture of the fiber optic bundle;

optically coupling the fiber optic bundle to the sample through a distal exit aperture of the fiber optic bundle remote from the scanner; and distancing a fundamental mode light image from ghost images which are produced by other modes by avoiding any overlap of the fundamental mode light image and ghost image by means of providing a predetermined optical length of the fiber optic bundle.

17. The improvement of claim 16 where optically coupling the sample arm through the scanner to a fiber optic bundle comprises coupling the sample arm through the scanner to a plurality of separate single mode or multimode fiber cores by focusing a scanning light beam onto the proximal entrance aperture of the fiber optic bundle.

18. The improvement of claim 16 where optically coupling the fiber optic bundle to the sample comprises focusing light onto the sample from the distal exit aperture of the fiber optic bundle through objective optics.

19. The improvement of claim 17 where coupling the sample arm through the scanner to a plurality of separate single mode or multimode fiber cores comprises:

maintaining relative spatial relationship between the plurality of cores comprising the fiber optic bundle between the proximal entrance aperture and the distal exit aperture of the optic fiber bundle;

providing a light source characterized by a coherence length and an objective optics coupling light between the distal exit aperture of the fiber optic bundle and the sample; and maintaining the relative spatial relationship of the light focused by the objective optics onto the sample from the distal exit aperture when focused onto the sample to spatially correspond to an individual fiber scanning position on the proximal entrance aperture of the fiber optic bundle.

20. The improvement of claim 17 where coupling the sample arm through the scanner to a plurality of separate single mode or multimode fiber cores comprises coupling only low-order modes to the plurality of separate single mode or multimode fiber cores and propagating only low-order modes in each core by setting the numerical aperture of the scanning optics to a magnitude less than the numerical aperture of each core in the fiber optic bundle.

21. The improvement of claim 16 further comprising reducing reflections from the proximal entrance aperture and distal exit aperture by polishing the entrance aperture and exit aperture at a predetermined angle.

22. The improvement of claim 16 further comprising reducing reflections from the proximal entrance aperture and distal exit aperture by polishing the entrance aperture and exit aperture at an angle of approximately 8° inclined relative to a perpendicular aperture face.

23. The improvement of claim 16 where distancing a fundamental mode light image from ghost images comprises positioning the ghost images out of the field of view of the fundamental mode light image by means of providing a predetermined optical length of the fiber optic bundle.

24. The improvement of claim 17 where each core is characterized by a fiber core size and where coupling the sample arm through the scanner to a plurality of separate single mode or multimode fiber cores comprises providing a scanning beam characterized by a beam size which is less than the fiber core size to improve coupling of the scanning beam into each core during scanning.

25. The improvement of claim 16 further comprising improving coupling efficiency between the scanner and fiber optic bundle.

26. The improvement of claim 25 where scanner and the fiber optic bundle are each characterized by a corresponding numerical aperture and improving coupling efficiency comprises matching the numerical aperture of the scanner and the fiber optic bundle, optimizing the scanning optics and the objective optics, or matching index of refraction between optical component connections between the scanner, fiber optic bundle, and objective optics.

* * * * *